(12) United States Patent
Baksh

(10) Patent No.: US 8,895,060 B2
(45) Date of Patent: *Nov. 25, 2014

(54) METHODS AND APPARATUS FOR SEALING CAPSULES

(75) Inventor: Bing Baksh, Placentia, CA (US)

(73) Assignee: Vita-Herb Nutriceuticals, Inc., Placentia, CA (US)

( * ) Notice: Subject to any disclaimer, the term of this patent is extended or adjusted under 35 U.S.C. 154(b) by 577 days.

This patent is subject to a terminal disclaimer.

(21) Appl. No.: 11/581,763

(22) Filed: Oct. 16, 2006

(65) Prior Publication Data

US 2007/0065502 A1   Mar. 22, 2007

Related U.S. Application Data

(60) Continuation-in-part of application No. 11/386,159, filed on Mar. 21, 2006, which is a division of application No. 10/672,668, filed on Sep. 26, 2003, now Pat. No. 7,214,370.

(60) Provisional application No. 60/414,083, filed on Sep. 26, 2002.

(51) Int. Cl.

| | | |
|---|---|---|
| A61K 9/48 | (2006.01) |
| A61K 38/44 | (2006.01) |
| A01N 63/00 | (2006.01) |
| C12N 1/12 | (2006.01) |
| C12N 1/20 | (2006.01) |
| C12P 1/04 | (2006.01) |
| A61K 36/13 | (2006.01) |
| A61K 36/42 | (2006.01) |
| A61K 36/53 | (2006.01) |
| A61K 36/61 | (2006.01) |
| A61K 36/736 | (2006.01) |
| A61K 36/752 | (2006.01) |
| A61K 36/8962 | (2006.01) |
| A61K 36/906 | (2006.01) |

(52) U.S. Cl.
CPC ............. *A61K 36/13* (2013.01); *A61K 9/4833* (2013.01); *A61K 9/4883* (2013.01); *A61K 36/42* (2013.01); *A61K 36/53* (2013.01); *A61K 36/61* (2013.01); *A61K 36/736* (2013.01); *A61K 36/752* (2013.01); *A61K 36/8962* (2013.01); *A61K 36/906* (2013.01); *Y10S 435/822* (2013.01); *Y10S 435/853* (2013.01)
USPC ....... 424/454; 424/93.4; 424/93.45; 435/170; 435/252.1; 435/822; 435/853

(58) Field of Classification Search
None
See application file for complete search history.

(56) References Cited

U.S. PATENT DOCUMENTS

| 4,539,060 A | 9/1985 | Wittwer |
| 4,647,433 A * | 3/1987 | Spector .................... 422/125 |
| 5,401,513 A * | 3/1995 | Wehling et al. .............. 424/464 |
| 5,635,609 A * | 6/1997 | Levy et al. .................. 536/2 |
| 2002/0081330 A1* | 6/2002 | Young ........................ 424/451 |

OTHER PUBLICATIONS

Capsugel CFS 1000 Capsule Liquid Filling & Sealing Machine document (two pages).

* cited by examiner

*Primary Examiner* — Debbie K Ware
(74) *Attorney, Agent, or Firm* — Cotman IP Law Group, PLC

(57) ABSTRACT

Methods and apparatus for providing a leak-proof seal for two-piece capsules containing oil-based liquids or other compositions by a two-stage process. The capsule cap and capsule body are combined by a nitrogen purge instant bonding (NPIB) system. An overlay medium is applied to selected portions of the capsule, including near the seam formed by the interconnection of the capsule cap and capsule body to provide a substantially leak-proof seal. The overlay medium is made from materials that make up the capsule cap and capsule body, including gelatin, starch, cellulose or polysaccharides, among others, which are dispersed in a hydro-alcoholic, aqueous or organic solution. The overlay medium includes additives to impart desired qualities to the capsule and include taste-enhancers, taste-maskers, odor-enhancers and odor-maskers. The additives may include color additives, aroma additives and taste additives.

14 Claims, 1 Drawing Sheet

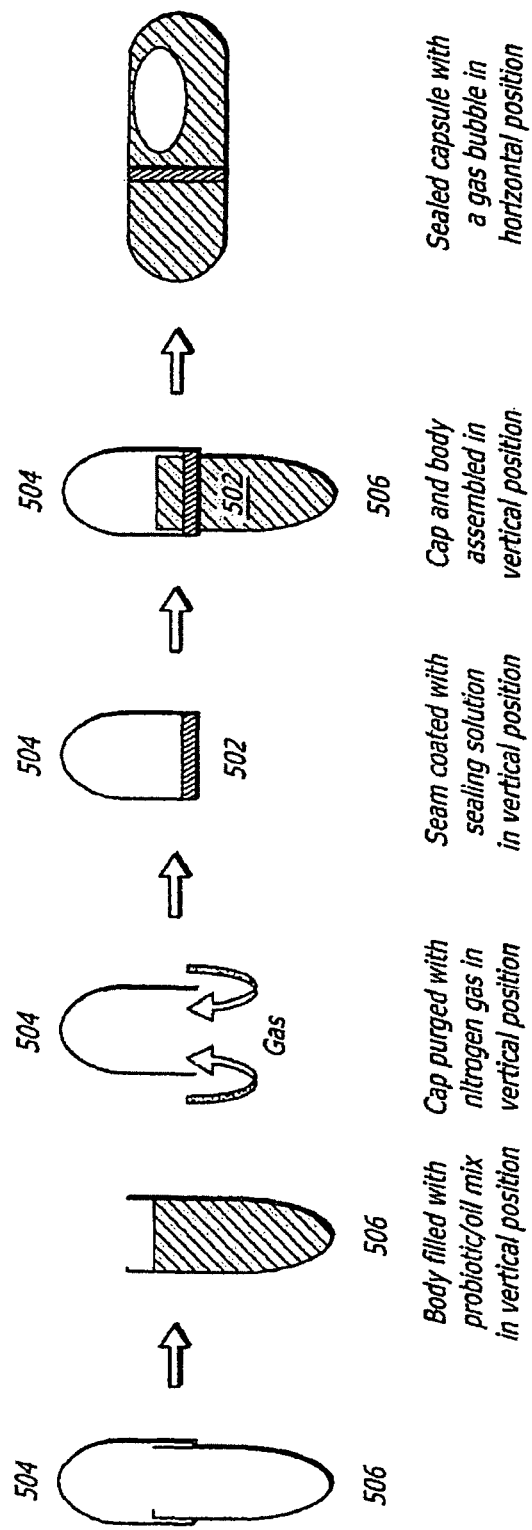

METHODS AND APPARATUS FOR SEALING CAPSULES

RELATED APPLICATION DATA

The present invention is a continuation-in-part of U.S. patent application Ser. No. 11/386,159 filed Mar. 21, 2006 which is a division of U.S. patent application Ser. No. 10/672,668 filed Sep. 26, 2003, now U.S. Pat. No. 7,214,370, which claims priority to U.S. provisional patent application Ser. No. 60/414,083 filed Sep. 26, 2002, the contents of which are incorporated by reference herein in their entirety.

BACKGROUND OF THE INVENTION

1. Field of the Invention

The invention relates generally to the field of sealing two-piece capsules and is more particularly, but not by way of limitation, directed to methods and apparatus for providing a leak-proof seal for oil-based liquids and compositions packaged in anaerobic encapsulation systems.

2. Description of the Related Art

Probiotics are microbial-based dietary adjuvants that beneficially affect the host physiology by modulating mucosal and systemic immunity, as well as improving nutritional and microbial balance in the intestinal tract {Naidu A S et al. Probiotic spectra of lactic acid bacteria (LAB). Crit. Rev. Food Sci. Nutr. 39:3-126, 1999]. Lactic acid bacteria (LAB) are indigenous probiotic microflora of mammalian gastrointestinal tract that play an important role in the host microecology and have been credited with an impressive list of therapeutic and prophylactic properties [Naidu A S, Clemens R A Probiotics, p. 431-462. In A S Naidu (ed.), Natural Food Antimicrobial Systems. CRC Press, Boca Raton, Fla., 2000]. These therapeutic and prophylactic properties include, but are not limited to the maintenance of microbial ecology of the gut, physiological, immuno-modulatory and antimicrobial effects [Gibson G R et al., Probiotics and intestinal infections, p. 10-39. In R. Fuller (ed.), Probiotics 2: Applications and practical aspects. Chapman and Hall, London, UK, 1997]. Other LAB associated attributes include enzyme release into the intestinal lumen that act synergistic with LAB adhesion to alleviate symptoms of intestinal malabsorption. Furthermore, the LAB-released enzymes help regulate intestinal pH that results in increased aromatic amino acid degradation [Mitsuoka T. Taxonomy and ecology pf bifidobacteria. Bifidobacteria Microflora 3:11, 1984]. LAB have also demonstrated the ability to significantly reduce sulfide and ammonia containing compounds in animal fecal waste and thus reduce the odor and toxicity associated with animal excrements [Niadu A S et al., Reduction of sulfide, ammonia compounds and adhesion properties of *Lactobacillus casei* strain KE99 in vitro. Curr. Microbiol. 44:196-205, 2002].

However, the greatest potential for LAB to improve life quality for man and domestic animals lies in their in vivo probiotic applications. In order for LAB to exhibit beneficial probiotic effects in vivo, the organisms must survive for extended time periods in the gut. Therefore, it is critical that probiotic LAB strains be selected that possess qualities that prevent their rapid removal by gut contraction [Havenaar R et al., Selection of strains for probiotic use, p. 209-224. In R. Fuller (ed.), Probiotics, the scientific basis. Chapman and Hall, London, UK, 1992]. Effective probiotic bacteria should be able to survive gastric conditions and colonize the intestine, at least temporarily, by adhering to the intestinal epithelia [Conway P. Selection criteria for probiotic microorganisms. Asia pacific J. Clin. Nutr. 5:10-14, 1996].

Furthermore, in addition to increasing in vivo viability and gastrointestinal tract life span, prolonged shelf life at room temperature remains a commercial challenge. Lactic acid bacilli generally require an effective delivery system that retains probio-functional activities (i.e. gut adhesion/retention, production of bacteriocins/enzymes) after their revival [Salminen S et al., Clinical uses of probiotics for stabilizing the gut mucosal barrier: successful strains and future challenges. Antonie Van Leeuwenhoek 70:347-3581, 1996]. Though freeze-drying is an effective process for preservation and delivery of probiotics, several physico-chemical factors such as humidity, aeration (oxygen availability) and temperature could compromise the cell viability, thereby the shelf life.

One potential additive class that may increase both in vivo life span and storage shelf-life is prebiotics. Prebiotics are non-digestible, or partially digestible, food ingredients that beneficially affect the host by selectively simulating the growth and/or activity of one or a limited number of bacterial species and thus in effect improve host health. [Gibson G R, Roberfroid M B. Dietary modulation of the human colonic microbiota: Introducing the concept of prebiotics. J. Nutr. 125:1401-12, 1995]. Intake of prebiotics can beneficially modulate probiotic LAB. Non-digestible oligosaccharides such as dietary fiber in general, and fructo-oligosaccharides (FOS) in particular, are well known prebiotics [Robrefroid M B. Health benefits of non-digestible oligosaccharides. Adv. Exp. Med. Biol. 427:211-0, 1997]. By combining the rationale of probiotics and prebiotics, the concept of 'synbiotics' is proposed to characterize some colonic foods with interesting nutritional properties in combination with health-enhancing functional food ingredients [Fuller R, Gibson G R modification of the intestinal microflora using probiotics and prebiotics. Scand. J. Gastroenterol. Suppl. 222:28-31, 1997].

Essential oils are known as biological preservatives due to their low water activity and limited air diffusion. Several essential oils also known to provide various nutraceutical benefits including antioxidant, antimicrobial, antitumor, and immune-modulatory activities. However, the prebiotic effects of essential oils on probiotic LAB are hereto fore unknown. Therefore, there remains a need to enhance probiotic activity, in vivo viability and shelf life of probiotic compositions including LAB.

One solution is the application of prebiotics in combination with advanced packaging methods. Currently, the hard shell capsule is a vehicle used to deliver various oil-based liquids used in the dietary supplement field. However, these capsules have been found to have persistent leaking problems. Several techniques exist that try to address capsule leaking. One technique uses viscosity enhancing agents added to the contents of the capsule, followed by an externally applied "band" (Capsule Banding) One technique is the novel Nitrogen Purge Instant Bonding (NPIB) system where, in one embodiment, the capsule cap is purged with nitrogen gas and the cap and body are sealed or bonded together. One technique applies a mist externally to the filled/snap-closed capsule, followed by vacuum removal of excess sealant, warm air drying, and temporary storage under vacuum to effect a seal (the LEMS system). All conventional techniques require time-consuming, expensive post-production treatments such as traying/visual inspection, washing/drying/visual inspection, among others. Until the present invention, leaking was a critical hurdle to be overcome so that liquid filled two-piece capsules can achieve widespread commercialization and consumer acceptance.

Thus, because of the above identified problems with conventional methods, a need exists for methods and apparatus that provide a leak-proof seal for capsules. There is also a need for additives that can be integrally bound to the sealed portion of the capsule to enhance visual appeal, to mask objectionable odors and tastes and to impart desirable odors and tastes.

BRIEF SUMMARY OF THE INVENTION

One or more embodiments of the invention are directed to methods and apparatus for providing a leak-proof seal for two-piece hard shell capsules containing oil-based liquids.

In one embodiment, the invention includes, but is not limited to, encapsulating one or more compositions within a capsule by a process using a Nitrogen-Purge Instant Bonding (NPIB) System. An overlay medium is thereafter applied to portions of the capsule, including the region formed by the connection between the cap and body. In a further embodiment, the overlay medium is a solution of hydro-alcoholic, aqueous or organic solvents that may or may not include similar materials that make up the cap and body dispersed into the solution. In one embodiment, the invention includes the capsule itself that is sealed and formed by the inventive process.

In further embodiments, the overlay medium includes one ore more additives. For example, the overlay medium can include color additives to enhance visual appeal or provide a visual warning or notice to patients. In one or more embodiments, the color additive may be one or more natural dyes or the color additive may be one or more artificial dyes.

In further embodiments, the overlay medium includes an aroma additive. In one embodiment, the additive may be one or more of the essential oils of orange, lemon, tangerine, peppermint, rosemary, wintergreen, anise, cardamom, cedar, sage, clove, eucalyptus, garlic, ginger, juniper, lavender, nutmeg, oregano, tarragon and thyme.

In another embodiment, the overlay medium includes a taste additive. The taste additive may be one or more of concentrated liquid fruit extracts or powdered fruit extracts of guava, orange, lemon, tangerine, watermelon, mango, banana, kiwi, peach, plum, pomegranate, nectarine and berry.

Other and further objects and advantages will be apparent to persons skilled in the art from the figures and written disclosure including the claims herein.

BRIEF DESCRIPTION OF THE DRAWINGS

Additional objects and features of the present invention will become more apparent and the invention itself will be best understood from the following Detailed Description, when read with reference to the accompanying drawings.

FIG. 1 depicts the process for making the anaerobic encapsulation system using the Nitrogen-Purge Instant Bonding (NPIB) system in accordance with the teachings of the present invention.

DETAILED DESCRIPTION OF THE INVENTION

The following descriptions of the preferred embodiment of the invention are exemplary, rather than limiting, and many variations and modifications are within the scope and spirit of the invention. Although numerous specific details and features are set forth in order to provide a thorough understanding of the present invention, it will be apparent to one of ordinary skill in the art, that embodiments of the invention may be practiced without these specific details or features. In other instances, well-known features have not been described in detail in order to avoid unnecessarily obscuring the present invention.

One or more embodiments of the invention are directed to methods and apparatus for sealing capsules by a two-step process. Probiotic lactobacilli require anaerobic or microaerobic conditions for optimum viability. Though oil immersion provides low water activity and limited oxygen diffusion, any evacuation of oxygen from the microenvironment would enhance the probiotic preservation. One embodiment of the invention includes an anaerobic encapsulation system using nitrogen-purge-instant-bonding (NPIB) to protect oil-emulsified probiotic formulations that are to be encapsulated. This process provides an optimal microenvironment (anaerobic/microaerophilic) condition ideal for probiotic bacteria. As used herein, the term "anaerobic" will mean a low oxygen tension environment and includes a strict anaerobic environment and microaerophilic environments. The NPIB system used in the present invention provides for oxygen displacement simultaneously with sealing the oil emulsified lactobacilli in a hard, two-piece capsule.

The NPIB system used in the present invention may also be used with other compositions including, but not limited to powders, oil-based liquids, oil-based suspensions, oil-based pastes, waxes, low-water content emulsions and a variety of bioactive compounds including, but not limited to lactoferrin, Moreover, the choice of capsular material is highly flexible. For example, in one embodiment of the invention, natural two piece hard gelatin capsules are used. In another embodiment hard vegetable capsules are used including starch, plant-derived cellulose and plant-derived polysaccharides. Additional capsule compositions include assorted synthetic and natural polymers known to persons skilled in the art. The NPIB system can be incorporated into any type of capsule filling equipment, including the manual, semi or fully automated as well as continuous or intermittent motion devices.

FIG. 1 illustrates one embodiment of an anaerobic encapsulation system used with the present invention. After separation of the cap 504 and body 506, an oil-based bioactive composition is added to the body 506 as shown in FIG. 1. An anaerobic gas, including, but not limited to, nitrogen or argon is injected into the capsule cap 504 and a sealing solution is applied to the inner, lower section of the cap at seam 502 as shown in FIG. 1. This results in instant bonding of the cap 504 and body 506 at the time when cap 504 and body 506 are joined during the closing step.

In one embodiment, the sealing solution is an aqueous-alcohol-cellulose solution comprising from approximately 50% to 99% ethanol, 90% being used in one embodiment (for vegetable capsules) or 10% to 70% isopropyl alcohol (IPA), 60% being used in one embodiment (for vegetable capsules), 15%-30% water being optimum for vegetable-based capsules, and 5-10 percent cellulose being optimum for vegetable capsules. However, those skilled in the art of formulation and filling technologies understand that other organic solutes/solvents are suitable at varying degrees of ethanol, isopropyl alcohol, solute and water.

The specific ratio of these four materials in a sealant is dependent on several factors such as (i) rate of sealant application, (ii) volume of sealant applied, (iii) method of sealant application, (iv) degree of sealant atomization, (v) method of atomization, and (vi) residence time. These factors are also strictly dependent on the wetability, solubility and softening properties of the capsular materials.

Accordingly, in one embodiment, the following conditions should be controlled during this sealing process: (a) the softening should not exceed the structural rigidity of the cap 504 during the closing step. Beyond a certain limit, the cap 504 deforms and fails to hold to the body 506; (b) the wet-ability and solubility properties of the cap 504 should be retained and effectively transferred to the body 506. This would allow proper fusion of the inner surface of the cap 504 with the outer surface of the body 506 during the closing step; (c) the cap 504 and body 506 should have excellent closure compatibility, since ethanol and isopropyl alcohol evaporate rapidly, while water evaporates slowly over a period of a few hours; and (d) the wet-ability and solubility properties are highly critical during the 'instant bonding' process. In one or more further embodiments of the invention, the nitrogen purge and sealing steps are done while the capsule is in a vertical position as shown in FIG. 1, although other and further positioning of the capsule are within the scope of the present invention.

Following the above, an overlay medium 30 is applied to selected portions of the capsule using methods and techniques well known to persons skilled in the art. In one embodiment, the overlay medium 30 is applied onto the capsule at or approximate to the surface area adjacent to the seam 502. In one or more embodiments, the overlay medium is a hydro-alcoholic solution, an aqueous solution or organic solvent solution that includes one or more of the materials that are common to the cap 504 and body 504 dispersed within the solution.

In one or more embodiments, the overlay medium 30 includes one or more additives, such as an enhancement additive or a masking additive. These additives are then bound to the capsule where the overlay medium is applied to produce the desired effect or effects. In one embodiment, the overlay medium 30 includes one or more color additives. Color additives include, but are not limited to, natural dyes, including carmine, chlorophyll, annato, turmeric, anthocyanins, beet, caramel, caratenoids and paprika oleoresins. In another embodiment, the color additive may be one or more artificial dyes including, but not limited to, FD&C Blue 11, Blue 2, Green 3, Red 3, Red 4, Red 40, Yellow 5 and Yellow 6.

In one or more embodiments, the overlay medium includes one or more aroma additives. These aroma additives include, but are not limited to, essential oils of orange, lemon, tangerine, peppermint, rosemary, wintergreen, anise, cardamom, cedar, sage, clove, eucalyptus, garlic, ginger, juniper, lavender, nutmeg, oregano, tarragon and thyme.

In one or more embodiments, the overlay medium includes one or more taste additives which include, but are not limited to, concentrated liquid or powdered fruit extracts of guava, orange, lemon, tangerine, watermelon, mango, banana, kiwi, peach, plum, pomegranate, nectarine and berry.

From the foregoing, a method and apparatus for sealing capsules have been disclosed. While the invention has been described with reference to specific embodiments and specific features, the description herein is illustrative of the invention and is not to be construed as limiting the invention to particular embodiments or combination of features. Numerous modifications, applications and variations may occur to persons skilled in the art without departing from the true spirit and scope of the invention. The inventor expects skilled persons to employ such modifications, applications and variations as appropriate and the inventor intends for the invention to be practiced other than specifically described herein. Accordingly, the invention includes all modifications and equivalents of the subject matter recited in the claims appended hereto as permitted by applicable law.

What is claimed is:

1. A method for the encapsulation of a composition within a capsule comprising:
   purging a capsule cap with a gas by injecting said gas into said capsule cap;
   coating a seam of said capsule cap with a sealing solution;
   sealing a capsule body to said capsule cap to form a capsule by securing said capsule cap to said capsule body in a vertical position to produce an instant bonding at said seam; and
   applying an overlay medium solution to selected portions of said capsule.

2. The method of claim 1 where said capsule cap and said capsule body comprise gelatin, starch, plant-derived cellulose or plant-derived polysaccharides.

3. The method of claim 1 where said overlay medium solution comprises at least one similar material of said capsule dispersed in a hydro-alcoholic, aqueous or organic solvent solution.

4. The method of claim 1 wherein said overlay medium solution comprises a color additive.

5. The method of claim 4 where said color additive is selected from the group consisting of natural dyes and artificial dyes.

6. The method of claim 1 where said overly medium solution comprises an aroma additive.

7. The method of claim 6 where said aroma additive is selected from the group consisting of essential oils of orange, lemon, tangerine, peppermint, rosemary, wintergreen, anise, cardamom, cedar, sage, clove, eucalyptus, garlic, ginger, juniper, lavender, nutmeg, oregano, tarragon and thyme.

8. The method of claim 1 where said overlay medium solution comprises a taste additive.

9. The method of claim 8 where said taste additive is selected from the group consisting of concentrated liquid fruit extracts of orange, lemon, tangerine, watermelon, mango, banana, kiwi, peach, plum, pomegranate, nectarine and berry.

10. The method of claim 8 where said taste additive is selected from the group consisting of powdered fruit extracts of orange, lemon, tangerine, watermelon, mango, banana, kiwi, peach, plum, pomegranate, nectarine and berry.

11. The method of claim 1 wherein said composition comprises an oil-emulsified probiotic formulation.

12. The method of claim 11 wherein said composition further comprises lactobacilli.

13. The method of claim 1 wherein said gas comprises an anaerobic gas.

14. The method of claim 13 wherein said anaerobic gas is nitrogen or argon.

* * * * *